US00PP11948P2

(12) United States Plant Patent
Booman

(10) Patent No.: US PP11,948 P2
(45) Date of Patent: Jun. 19, 2001

(54) BEGONIA PLANT NAMED 'NEW YORK SWIRL'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 09/375,784

(22) Filed: Aug. 17, 1999

(51) Int. Cl.[7] ..... A01H 5/00
(52) U.S. Cl. ..... Plt./343

(58) Field of Search ..... Plt./343

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Rex Begonia plant named 'New York Swirl', characterized by its uniform growth habit; moderate plant vigor; no requirement for winter dormancy; and interesting and attractive leaf coloration and pattern.

1 Drawing Sheet

BACKGROUND OF THE INVENTION

The present invention relates to a new and distinct cultivar of Begonia plant, botanically known as *Begonia rex* hybrid, commercially known as Rex Begonia, and hereinafter referred to by the name 'New York Swirl'.

The new Rex Begonia was discovered by the Inventor in a controlled environment in Vista, Calif., in August, 1996, as a naturally-occurring mutation of *Begonia rex* hybrid 'Lalome', not patented. The new Rex Begonia was observed as a single plant in a group of plants of the parent cultivar. The selection of this plant was based on its unique leaf coloration and pattern.

Asexual reproduction of the new Rex Begonia by leaf cuttings taken in a controlled environment in Vista, Calif., has shown that the unique features of this new Rex Begonia are stable and reproduced true to type in successive generations.

SUMMARY OF THE INVENTION

The cultivar 'New York Swirl' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'New York Swirl'. These characteristics in combination distinguish 'New York Swirl' as a new and distinct Rex Begonia:

1. Uniform growth habit.
2. Moderate plant vigor.
3. Does not require winter dormancy.
4. Stable, interesting and attractive leaf coloration and pattern.
5. Consistent "corkscrew" leaf formation.

Compared to plants of the parent cultivar Lalome, zonation patterns on leaves of the new Rex Begonia are more distinct and stable.

In side-by-side comparisons conducted by the Inventor in Vista, Calif., plants of the new Rex Begonia differ from plants of the nonpatented cultivar 'Merry Christmas Corkscrew' in the following characteristics:

1. Plants of the new Rex Begonia grow more rapidly than plants of the cultivar 'Merry Christmas Corkscrew'.
2. Plants of the new Rex Begonia have larger and fuller leaves than plants of the cultivar 'Merry Christmas Corkscrew'.
3. Leaves of plants of the new Rex Begonia and the cultivar 'Merry Christmas Corkscrew' differ in coloration and pattern.
4. Plants of the new Rex Begonia do not require a winter dormancy period whereas plants of the cultivar 'Merry Christmas Corkscrew' do require a winter dormancy period.

In side-by-side comparisons conducted by the Inventor in Vista, Calif., plants of the Rex Begonia differ from plants of the nonpatented cultivar 'Lillium' in the following characteristics:

1. Plants of the new Rex Begonia have flatter and larger leaves than plants of the cultivar 'Lillium'.
2. Leaves of plants of the new Rex Begonia have a "corkscrew" formation whereas leaves of plants of the cultivar 'Lillium' do not have a "corkscrew" formation.
3. Plants of the new Rex Begonia do not require a winter dormancy period whereas plants of the cultivar 'Lillium' do require a winter dormancy period.

BRIEF DESCRIPTION OF THE PHOTOGRAPH

The accompanying colored photograph illustrates the overall appearance of the new Rex Begonia, showing the colors as true as it is reasonably possible to obtain in colored reproductions of this type. The photograph comprises a top perspective view of a typical plant of 'New York Swirl'. Foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown during the spring in Vista, Calif., under conditions which approximate commercial practice. Plants used for this description were grown in 15-cm containers for about 3 months.

Botanical classification: *Begonia rex* hybrid cultivar 'New York Swirl'.

Commercial classification: Rex Begonia.

Parentage: Naturally-occurring mutation of *Begonia rex* hybrid 'Lalome', not patented.

Propagation:

*Type.*—Leaf cuttings.

*Time to initiate roots, summer.*—About 56 days at 21° C.

*Time to initiate roots, winter.*—About 56 days at 21° C.

*Time to develop roots, summer.*—About 84 days at 21° C.

*Time to develop roots, winter.*—About 98 days at 21° C.

*Rooting habit.*—Fine, fibrous and well-branched.

Plant description:

*Plant form.*—Rosette; compact; dense and outwardly arching potted plant; freely basal branching with good leaf petiole strength.

*Vigor.*—Moderate.

*Plant height, soil surface to top of leaf canopy.*—About 26 cm.

*Plant width.*—About 67 cm.

*Leaves.*—Arrangement: Simple. Length: Petiole to apex: About 15.5 cm. Base to apex: About 24 cm. Width: About 20.5 cm. Shape: Ovate, somewhat cordate; central "corkscrew" formation. Apex: Young, acute; mature, obtuse. Base: Overlapping cordate, "corkscrew" formation. Margin: Somewhat pectinate; irregularly undulate. Texture: Leathery, rugose; pubescence on lower surface veins. Color: Young foliage, upper surface: Margin: 187A with small areas of 143B. Central venal areas: 200A to 200B, merging into 183A. Blade to margin: Iridescent, 148D. Young foliage, lower surface: Margin: 183A. Central venal areas: 183A. Background: 147C. Mature, fully expanded, foliage, upper surface: Margin: Dark brown, 200A, with irregular patches of 144A. Central venal areas: 200D spreading into metallic 185B and 185D. Blade to antemarginal: Iridescent, close to 191C. Veins: 166A. Mature, fully expanded, foliage, lower surface: Margin: 183A. Central venal area: 183A. Background: 148C. Veins: 187A; reticulate.

*Petioles.*—Length: About 20 cm. Diameter: About 9 mm. Shape: Longitudinally grooved. Texture: Pubescent. Color: 178B.

*Stipules.*—Length: About 1.85 cm. Diameter at base: About 1.25 cm. Shape: Subulate, deltoid. Color: Close to 42A.

Flower description:

*Flowering habit.*—Male flowers, single with one whorl of four tepals. Female flowers, semi-double with three tepals interior to outer whorl of five tepals. Usually about three flowers per cyme. Flowers persistent.

*Natural flowering season.*—Plants will flower continuously, but typically plants flower more abundantly during the spring and summer.

*Flowers.*—Shape: Rounded; somewhat cup-shaped. Diameter: About 4 cm. Depth (height): About 2.1 cm. Aspect: Drooping about 45° from vertical. Fragrance: None.

*Flower buds.*—Shape: Ovoid; bulbous with marginal lip. Length: About 11.7 mm. Diameter: About 9 mm. Color: Iridescent, close to 50B; lip, 55A.

*Tepals.*—Arrangement: Rosette. Length: About 1.75 cm. Width: About 1.25 cm. Shape: Ovate with obtuse apex. Margin: Entire. Texture: Smooth, waxy; iridescent, translucent. Color: When opening, upper surface: 55B to 55D. When opening, lower surface: 55A to 55D. Fully opened, upper surface: 55B to 55D. Fully opened, lower surface: 55A to 55D.

*Peduncles.*—Angle: About 40° from vertical. Length: About 4 cm. Diameter: About 2 mm. Strength: Firm. Texture: Smooth, waxy. Color: 146C.

*Pedicels.*—Angle: About 40° from vertical. Length: About 1.5 cm. Diameter: About 1.5 mm. Strength: Flexible, moderately weak. Texture: Smooth, waxy. Color: 38A.

*Reproductive organs.*—Male flowers: Stamen quantity: About 88, globose mass. Anther shape: Rhomboidal; lower sides curved inwardly. Anther length: About 2.5 mm. Filament length: About 1.5 mm. Anther color: 15A. Pollen: Not observed. Female flowers: Pistil length: About 2.1 cm. Stigma shape: Funnel; bilobate. Stigma color: 145C. Ovary: Inferior; three-winged; one large top wing, 180A, and two lower wings, both surfaces, 179A.

Disease resistance: Resistance to diseases common to Rex Begonia has not been determined.

Seed production: Seed production has not been observed.

It is claimed:

1. A new and distinct cultivar of Rex Begonia plant named 'New York Swirl', as illustrated and described.

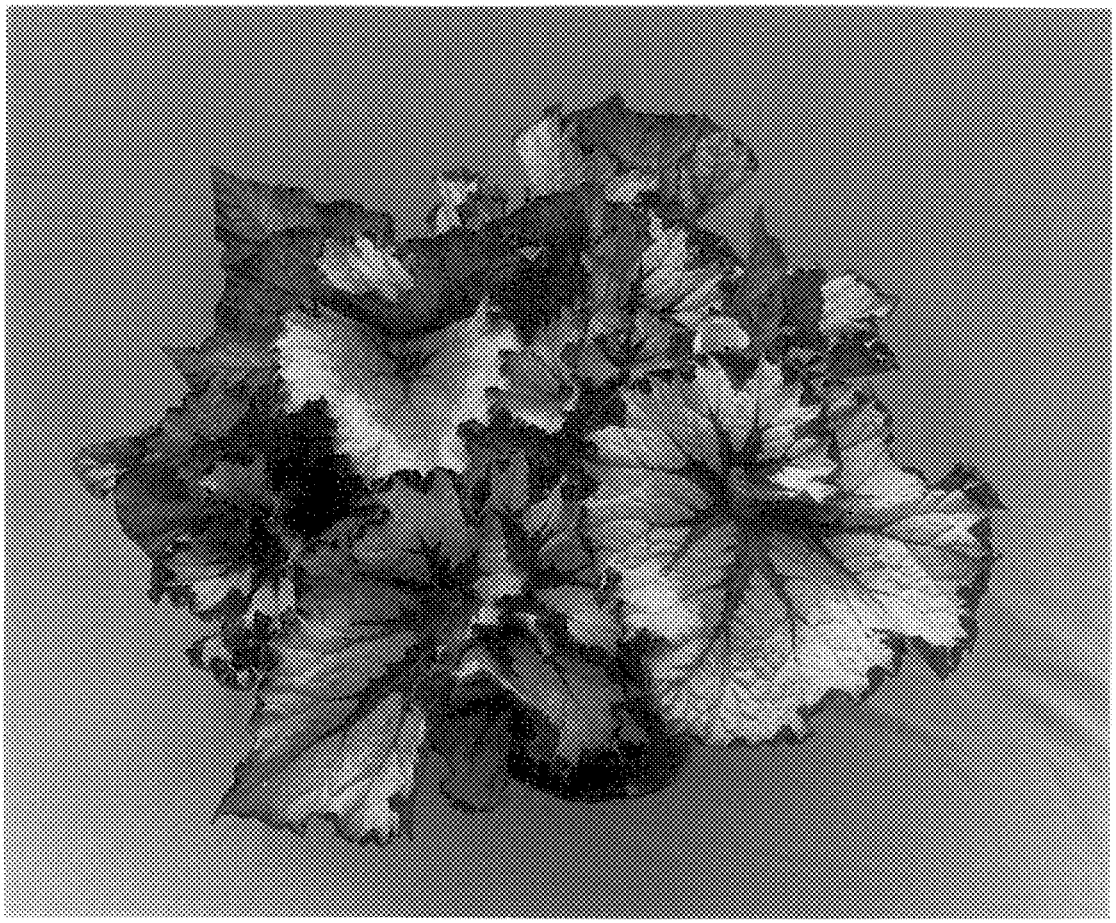

* * * * *